United States Patent
Piatek et al.

(10) Patent No.: US 6,761,312 B2
(45) Date of Patent: Jul. 13, 2004

(54) SYSTEM AND METHOD FOR TRACKING VICTIMS OF A MASS CASUALTY INCIDENT

(75) Inventors: John T. Piatek, Traverse City, MI (US); Russell L. Miller, Traverse City, MI (US); Michael A. Whelan, Traverse City, MI (US)

(73) Assignee: Salamander Technologies, Inc., Traverse City, MI (US)

( * ) Notice: Subject to any disclaimer, the term of this patent is extended or adjusted under 35 U.S.C. 154(b) by 0 days.

(21) Appl. No.: 10/170,781

(22) Filed: Jun. 12, 2002

(65) Prior Publication Data

US 2002/0153413 A1 Oct. 24, 2002

Related U.S. Application Data

(63) Continuation of application No. 09/628,635, filed on Jul. 31, 2000, now abandoned.
(60) Provisional application No. 60/146,629, filed on Jul. 30, 1999.

(51) Int. Cl.[7] .............................................. G06F 17/60
(52) U.S. Cl. ............. 235/385; 235/472.02; 235/462.01; 235/462.09; 235/462.45; 235/462.46; 705/2; 705/3
(58) Field of Search ........................... 235/375, 462.01, 235/462.09, 462.45, 462.46, 472.02, 492, 380, 382; 705/2, 3

(56) References Cited

U.S. PATENT DOCUMENTS

| | | | |
|---|---|---|---|
| 4,814,594 A | * 3/1989 | Drexler ..................... 235/487 |
| 5,291,399 A | * 3/1994 | Chaco ........................ 235/375 |
| 5,586,024 A | * 12/1996 | Shaibani ................. 364/413.02 |
| 5,595,507 A | * 1/1997 | Wilcox et al. .............. 345/112 |
| 5,596,652 A | 1/1997 | Piatek et al. |
| 5,635,012 A | * 6/1997 | Belluci et al. .............. 156/277 |
| 5,793,882 A | 8/1998 | Piatek et al. |
| 5,801,364 A | * 9/1998 | Kara et al. .................. 235/375 |
| 5,877,742 A | * 3/1999 | Klink ......................... 345/123 |
| 5,995,077 A | 11/1999 | Wilcox et al. |
| 6,029,889 A | * 2/2000 | Whalen, Jr. et al. ........ 235/380 |
| 6,084,513 A | 7/2000 | Stoffer |
| 6,179,358 B1 | * 1/2001 | Hirayama et al. .......... 296/24.1 |
| 6,305,605 B1 | 10/2001 | Goetz et al. |
| 6,499,658 B2 | * 12/2002 | Goetz et al. ................ 235/385 |

* cited by examiner

*Primary Examiner*—Michael G. Lee
*Assistant Examiner*—Ahshik Kim
(74) *Attorney, Agent, or Firm*—Price, Heneveld, Cooper, DeWitt & Litton

(57) ABSTRACT

A system and method for tracking victims of a mass casualty incident includes the steps of: (a) providing a tag to be associated with each victim, each tag containing machine-readable data representing information including at least the victims triage priority; (b) reading the machine-readable data; and (c) displaying the information read in step (b). Each tag may further contain machine-readable data representing information including at least one of (1) an identification code uniquely associated with the victim; (2) name of the victim; (3) the nature of the victim's injuries; (4) the victim's medical condition; (5) the victim's initial treatment; (6) physical characteristics of the victim; (7) the victim's photo; and (8) the location to which the victim was transported or assigned.

27 Claims, 2 Drawing Sheets

US 6,761,312 B2

SYSTEM AND METHOD FOR TRACKING VICTIMS OF A MASS CASUALTY INCIDENT

CROSS-REFERENCE TO RELATED APPLICATION

This application is a continuation of U.S. patent application Ser. No. 09/628,635, entitled "SYSTEM AND METHOD FOR TRACKING VICTIMS OF A MASS CASUALTY INCIDENT," filed on Jul. 31, 2000, now abandoned by John T. Piatek et al., which claims priority under 35 U.S.C. §119(e) on U.S. Provisional Application No. 60/146,629 entitled "SYSTEM AND METHOD FOR TRACKING VICTIMS OF A MASS CASUALTY INCIDENT," filed on Jul. 30, 1999, by John T. Piatek. The entire disclosure of each of these applications is incorporated herein by reference.

BACKGROUND OF THE INVENTION

The present invention generally pertains to a system and method for tracking victims of a mass casualty incident, and more particularly pertains to systems and methods for tracking victims utilizing portable data.

A mass casualty incident may arise from a natural disaster (i.e., tornado, earthquake, flood, etc.), emergency situations (i.e., hazardous material spills, fires, traffic accidents, plane crashes, etc.), or from terrorist activity. A mass casualty incident represents a major logistical challenge for emergency response personnel who, must locate, triage, treat, stage, transport, and deliver numerous victims to medical facilities or a morgue. Time is of the essence in the ability to ascertain the identification, status, and medical condition of the victims. During the emergency, disaster or incident, traditional data/communication field systems (such as telephone, cellular, RF transmissions, etc.) could be "down" or overloaded, suggesting the prudence of having an alternative or supplementary method of data communication.

SUMMARY OF THE INVENTION

An aspect of the present invention is to provide a mobile, field-deployable system used during an emergency, disaster, terrorist attack, or other mass casualty incident. This system creates high capacity, machine-readable media (such as PDF417 barcodes) which are transportable with the victim to provide such information as: physical characteristics; nature of injury; medical condition; triage priority; initial treatment; sample data (physical or environmental); photo; and like or similar information that is relevant to the identification, treatment, or disposition of a victim. It is another aspect of the present invention to provide machine-readable information that can be read by "downstream" agencies or care providers such as staging areas, EMS ambulances or other transporters, hospitals, morgues, test facilities, etc. to assist in the identification, treatment, or disposition of the victim.

The use of portable data tags is extremely beneficial when normal communication systems are non-functional. Also, because time is of the essence in treating victims, the flow and accessibility of such critical information is very important so as to prevent many triage tasks from being repeated.

These and other features, advantages, and objects of the present invention will be further understood and appreciated by those skilled in the art by reference to the following specification, claims, and appended drawings.

DETAILED DESCRIPTION OF PREFERRED EMBODIMENT

As mentioned above and explained in more detail below, the present invention relates to a system and method for tracking victims of a mass casualty incident and, more generally, for maintaining information pertaining to the victims. The method includes the steps of providing a tag associated with each victim that contains machine-readable data representing certain information, reading the machine-readable data, and displaying the information read from the machine-readable data. The information represented by the machine-readable data on the tag associated with each victim includes at least one of: (1) an identification code uniquely associated with the victim; (2) name of the victim; (3) the nature of the victim's injuries; (4) the victim's medical condition; (5) the victim's triage priority; (6) the victim's initial treatment; (7) physical characteristics of the victim; (8) the victim's photo; and (9) the location to which the victim was transported or assigned.

The machine-readable data printed on the tag associated with the victim may take many different forms. For example, the machine-readable data may be contained in a radio frequency (RF) or infrared (IR) signal transmitted from a transmitter attached to the victim, or to a medical apparatus or device associated with the victim, or may be stored electronically or magnetically and retrieved using an appropriate reading device. Hence, the tag may include an RF or IR transmitter, smart card, smart button, or RF identification chip. Preferably, the machine-readable data is presented in the form of two-dimensional symbology, such as PDF417, in which the victim tag includes a label having the machine-readable data printed on it.

Figure 1:
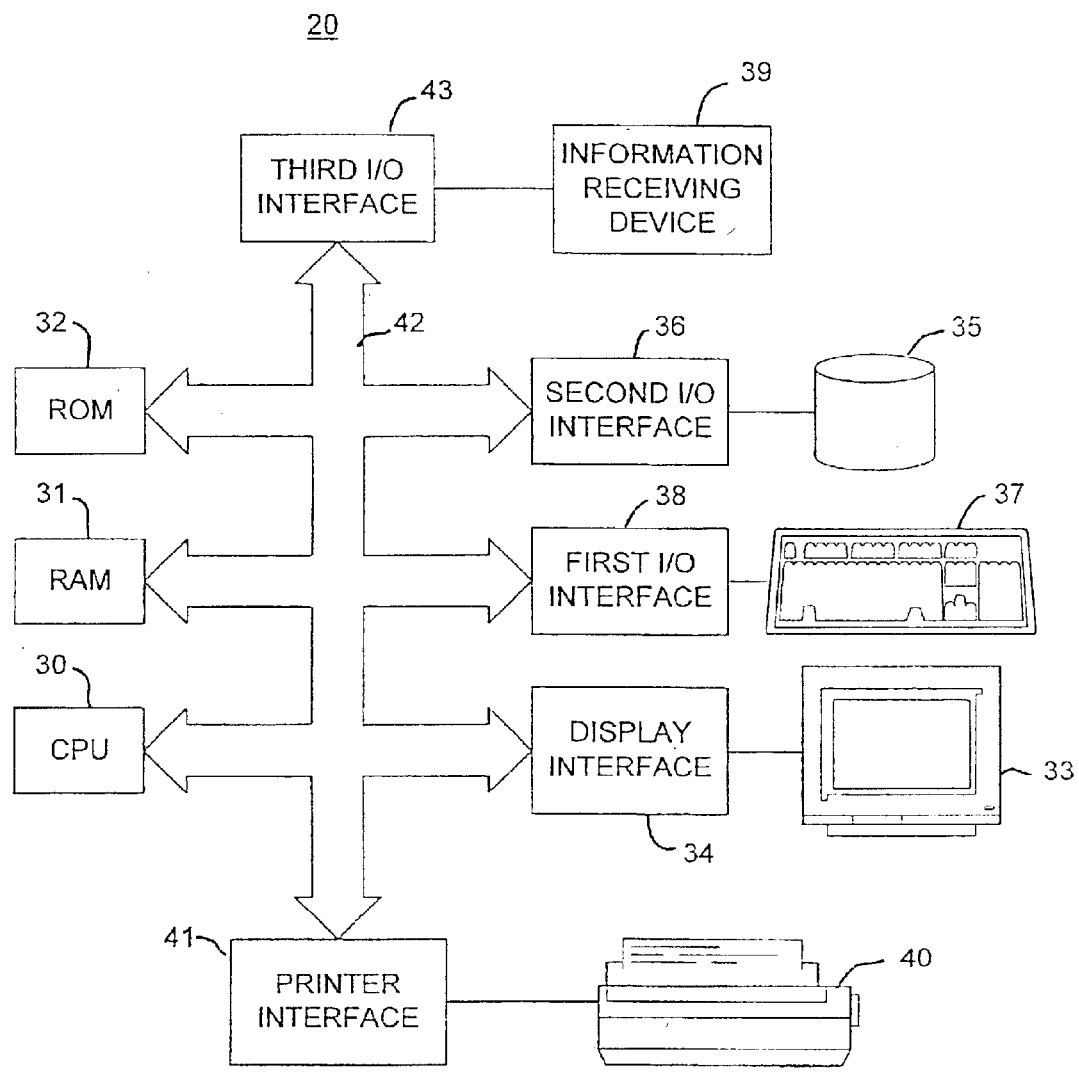
FIG. 1 is a system diagram in block form of a system constructed in accordance with the present invention.

FIG. 1 shows an example of one computer hardware system 20 that may be used, in whole or in part, to implement the various embodiments of the victim tracking system of the present invention. As shown in FIG. 1, computer hardware system 20 includes a central processing unit (CPU) 30; a random access memory (RAM) 31; a read only memory (ROM) 32; a display monitor 33; a display interface 34 connected to display monitor 33; a data storage device 35; a first input/output (I/O) interface 36 connected to data storage device 35; a keyboard 37; a second I/O interface 38 connected to keyboard 37; an information receiving device 39 connected to a third I/O interface 43; a printer 40; a printer interface 41 connected to printer 40; and a system bus 42 for interconnecting CPU 30, RAM 31, ROM 32, display interface 34, first I/O interface 36, second I/O interface 38, and printer interface 41. As described below, information receiver 39 may take any appropriate form for receiving data from the particular form of machine-readable data used for the particular embodiment or for receiving machine-recognizable information that may be processed by a computer. Preferably, data storage device 35 is a computer hard disk drive.

As will be apparent to those of ordinary skill in the art, the components of computer hardware system 20 may be incorporated into a personal computer or a portable laptop computer, with the possible exception of information receiver 39 and printer 40. However, as will become apparent from the following description of the present invention, certain components of computer hardware system 20 may be eliminated depending upon the manner in which it is used within the confines of the present invention. For example, if computer hardware system 20 were used solely for producing and storing the data associated with the victim, information receiver 39 may be eliminated. On the other hand, if computer hardware system 20 were used solely for receiving data and displaying the received data, keyboard 37 may be eliminated and printer 40 would become optional, unless one wished to print out information displayed on display monitor 33. By eliminating keyboard 37 and/or printer 40, computer hardware system 20 may be implemented in a very portable, small integral device. Clearly, the particular form taken by computer hardware system 20 will depend upon the manner and environment in which the system is used. Further, computer system 20 may also be configured with a cellular telephone, a global positioning system (GPS), digital camera, facsimile machine, image scanner, or fax/modem.

The system may also include a portable power source such as a rechargeable battery so that the system may receive power in the event of a local power failure, which may accompany such mass casualty events. As will be apparent, the transportability of the system and the data associated with the victims may be critical when the mass casualty event has caused power failures and break downs of the communication systems (telephone lines and towers and radio communication systems) that would otherwise be in place.

Figure 2:
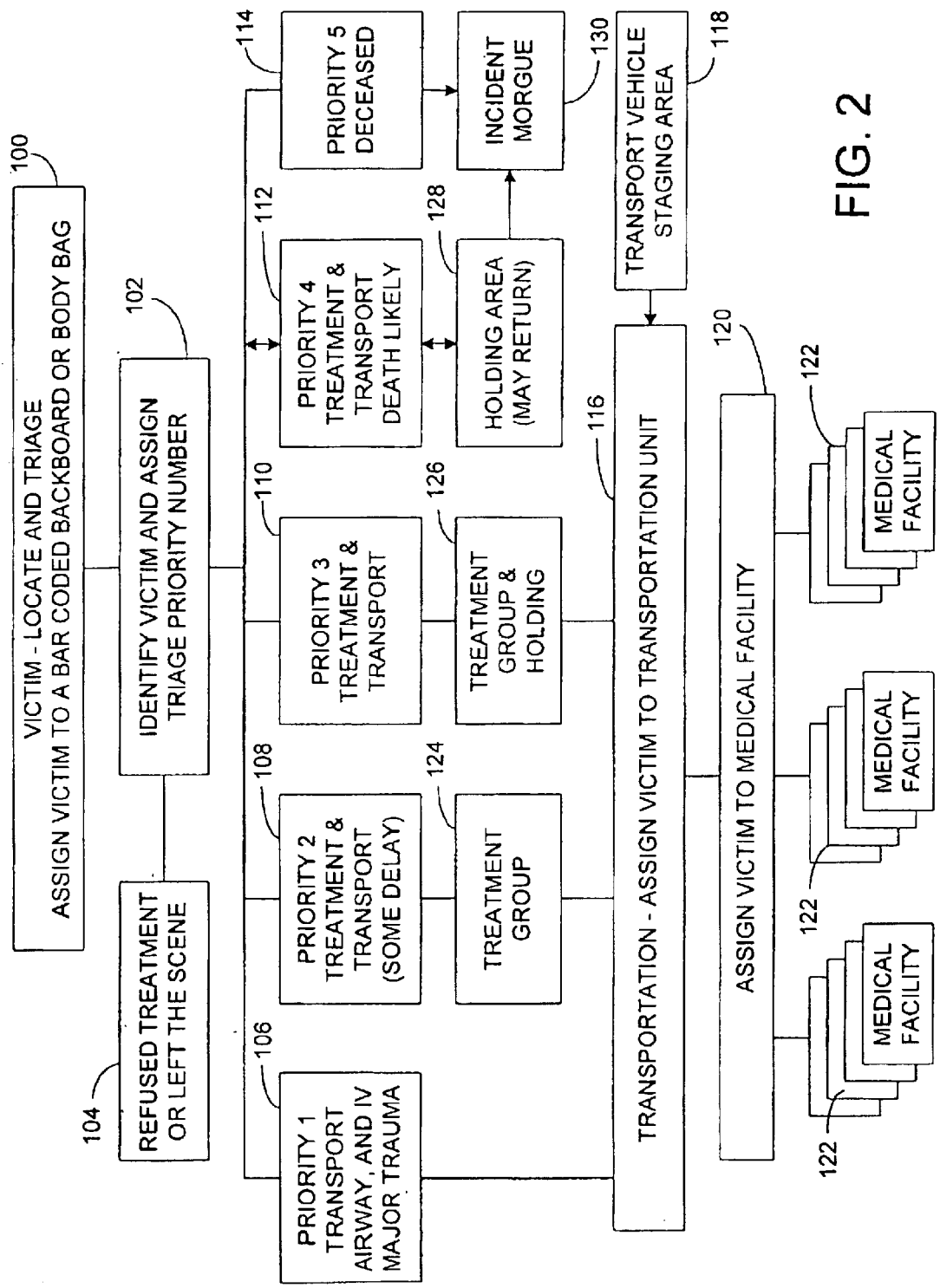
FIG. 2 is a flow chart illustrating a general flow of operations utilizing machine-readable data in accordance with the present invention.

FIG. 2 illustrates but one example of how the present invention may be employed to process and track victims of a mass casualty incident. The first step in treating victims of any mass casualty is to locate and triage the victims. In accordance with the principles of the present invention, as each victim is located, they are assigned to a backboard, gurney, bed, or body bag (block 100). Each such backboard, gurney, bed, or body bag would preferably include a pouch for maintaining a tag or otherwise have the tag affixed to this item. The tag would preferably be configured to carry one or more two-dimensional bar code labels that may be printed and releasably secured to the tag. Each such tag would include a two-dimensional bar code or the like, which uniquely identifies the body bag, gurney, or backboard. Such unique identification allows for initial tracking of the victim assigned to that article.

As indicated in block 102, the next step is to attempt to identify the victim and assign a priority number. Some of the "victims" may refuse treatment or leave the scene, as indicated in block 104, in which case they are not further processed. It should be noted that the primary purpose of the initial step is to assign a triage priority number, since the victims may be identified at subsequent steps. Particularly, if the victim is in the most critical condition, it is important to get that victim to the nearest medical facility without delay.

In general, each victim is assigned one of five priorities indicated with reference to blocks 106 through 114. Priority 1 (block 106) is reserved for the most critically injured and treatable victims. Priority 2 (block 108) is reserved for victims that are somewhat less critical than priority 1 victims, while the priority 3 indication (block 110) is reserved for victims whose injuries are less than those of the priority 2 victims. Priority 4 (block 112) is reserved for those victims whose injuries are so traumatic that death is imminent. Priority 5 (block 114) is reserved for victims who are deceased. Thus, when the victims are assigned a priority (block 102), the priority is printed onto a label that may be secured to the tag of the backboard, gurney, or body bag with which the victim is associated. Because priority 1 victims should be immediately transported to the appropriate medical facility, these victims may, at the same time, be assigned to a transportation unit (block 116) and to a medical facility 122 (block 120). These assignments may be printed onto a bar code that is affixed to the backboard or gurney associated with the victim.

Priority 2 victims may be temporarily maintained and treated by a treatment group 124 prior to transportation at a transport vehicle staging area 118 where they are assigned to a transport unit (block 116), and subsequently or simultaneously assigned to a medical facility 122 (block 120). Similarly, priority 3 victims may be held at a treatment group (block 126) prior to release or transport to a medical facility. Thus, priority 3 victims would be treated in a manner very similar to priority 2 victims, with the exception that they may have to wait longer to be transported to a medical facility.

Priority 4 victims are maintained in a holding area (block 128) where they may receive painkillers or other treatment. If it is subsequently determined that the victim is not facing imminent death, the victim may be returned and reassigned a different priority for treatment. On the other hand, if the priority 4 victim should become deceased, and hence a priority 5 victim, they are transported to the incident morgue (block 130). Any reassignment in priority would preferably be indicated in a new bar code that is printed and attached to the victims associated tag.

The bar codes for the priority number, transportation unit, and medical facility to which the victim may be assigned could be attached to the victim's associated tag and could also provide additional information such as the victim's physical characteristics, nature of injury, medical condition, initial treatment, data on samples (such as the victim's blood type, pulse, blood pressure, etc.), and the like or similar information which is relevant to the identification, treatment, or disposition of the victim. This additional information could be added to the existing information or separately added at any stage in the processing of the victims. Additional data may include the identification of any hazardous material with which the victim may have come into contact. Such information could prove extremely valuable to the doctors at the medical facilities who ultimately treat these victims. By providing such information as portable, machine-readable data, this information may be transported with the victim and read using standard equipment by any of those needing the information. Those who would read the information need not have access to any shared database to gain access to the information maintained in the associated bar codes or other high capacity medium. Thus, the present invention would be particularly advantageous in those conditions where there are disruptions in communications between emergency service vehicles, ambulances, and medical facilities.

Once the victim has arrived at a medical facility, those facilities may apply additional bar code labels to assist each medical facility in tracking the patients. Additionally further information about the victims/patients may be obtained, such as their medical history, blood type, and other conditions that may not have been obtained in the field.

It will be appreciated by those skilled in the art that different triage priority schemes may be used. For example, the number of priorities and definitions of the priorities may vary. It will also be appreciated that the broad methodology of the present invention may be applied regardless of the triage priority scheme that is used.

The above description is considered that of the preferred embodiment only. Modifications of the invention will occur to those skilled in the art and to those who make or use the invention. Therefore, it is understood that the embodiment shown in the drawings and described above is merely for illustrative purposes and not intended to limit the scope of the invention, which is defined by the following claims as interpreted according to the principles of patent law, including the doctrine of equivalents.

What is claimed is:

1. A method of tracking victims of a mass casualty incident comprising the steps of:
   (a) arriving on a scene of the mass casualty incident;
   (b) locating the victims and determining a triage priority for each of the victims, wherein the triage priority for each of the victims is determined relative to injuries suffered by the other victims;
   (c) providing a tag to be associated with each victim, each tag containing machine-readable data representing information including at least the victim's triage priority;
   (d) reading the machine-readable data; and
   (e) displaying the information read in step (d).

2. The method of claim 1 and further comprising the step of sorting and allocating treatment of the victims based on the triage priority stored in the machine-readable data.

3. The method of claim 1, wherein the machine-readable data is presented in the form of two-dimensional symbology.

4. The method of claim 1, wherein the machine-readable data is releasably secured to the tag.

5. The method of claim 1, wherein the triage priority stored in the machine-readable data is a number.

6. The method of claim 1, wherein the information represented by the machine-readable data further includes an identification code uniquely identifying the victim.

7. The method of claim 1 and further including the steps of:
   (f) re-evaluating the triage priority of at least some of the victims; and
   (g) providing on the tag updated machine-readable data representing information including at least the victim's updated triage priority.

8. The method of claim 1, wherein each said tag further contains machine-readable data representing information including at least one of: (1) an identification code uniquely associated with the victim; (2) name of the victim; (3) the nature of the victim's injuries; (4) the victim's medical condition; (5) the victim's initial treatment; (6) physical characteristics of the victim; (7) the victim's photo; and (8) the location to which the victim was transported or assigned.

9. A system for tracking victims of a mass casualty incident comprising:
   a plurality of tags each associated with a victim, each tag containing machine-readable data representing information including the victim's triage priority and at least one of: (1) an identification code uniquely associated with the victim; (2) the nature of the victim's injuries; (3) the victim's medical condition; (4) the victim's initial treatment; and (5) the location to which the victim was transported or assigned; and
   means for producing the machine-readable data for the tag for each victim after arrival at the mass casualty incident such that each victim's triage priority may be determined after evaluating the condition of the victim relative to the other victims.

10. The system of claim 9, wherein each tag contains machine-readable data representing information further including at least two of: (1) the nature of the victim's injuries; (2) the victim's medical condition; (3) the victim's initial treatment; and (4) the location to which the victim was transported or assigned.

11. The system of claim 9, wherein each tag contains machine-readable data representing information including: (1) the victim's triage priority; (2) the nature of the victim's injuries; (3) the victim's medical condition; (4) the victim's initial treatment; and (5) the location to which the victim was transported or assigned.

12. The system of claim 9, wherein each of said tags further includes machine-readable data representing information including at least one of: (6) an identification code uniquely associated with the victim; (7) name of the victim; (8) physical characteristics of the victim; and (9) the victim's photo.

13. The system of claim 9, wherein machine-readable data may be contained in a radio frequency or infrared signal transmitted from a transmitter attached to each said tag associated with a victim.

14. The system of claim 9, wherein said machine-readable data is electronically stored in said tags.

15. The system of claim 9, wherein said machine-readable data is magnetically stored in said tags.

16. The system of claim 9, wherein said tags include an RF or IR transmitter.

17. The system of claim 9, wherein said tags include a smart card.

18. The system of claim 9, wherein said tags include a smart button.

19. The system of claim 9, wherein said tags include an RF identification chip.

20. The system of claim 9, wherein said tags contain machine-readable data that is presented in the form of two-dimensional symbology.

21. The system of claim 20, wherein said two-dimensional symbology is PDF417.

22. The system of claim 9, and further including a data reader for reading said machine-readable data; and a display device for displaying the machine-readable data read by said data reader.

23. A system for tracking victims of a mass casualty incident comprising:
   a plurality of tags each associated with a victim, each tag containing machine-readable data representing information including at least one of: (1) the victim's triage priority; (2) the nature of the victim's injuries; (3) the victim's medical condition; (4) the victim's initial treatment; and (5) the location to which the victim was transported or assigned, wherein said tags contain machine-readable data that is presented in the form of two-dimensional symbology.

24. A method of sorting and allocating treatment of victims of a mass casualty incident comprising the steps of:
   (a) arriving on a scene of the mass casualty incident;
   (b) locating the victims and determining a triage priority for each of the victims relative to injuries suffered by the other victims;

(c) providing a tag to be associated with each victim, each tag containing machine-readable two-dimensional symbology representing information including at least a triage priority number representing the victim's triage priority and an identification code uniquely associated with the victim;

(d) reading the machine-readable two-dimensional symbology;

(e) displaying the information read in step (d);

(f) sorting and allocating treatment of the victims based on the triage priority number stored in the machine-readable two-dimensional symbology.

25. The method of claim 24, wherein the machine-readable two-dimensional symbology is releasably secured to the tag.

26. The method of claim 24 and further including the steps of:

(g) re-evaluating the triage priority of at least some of the victims; and (h) providing on the tag updated machine-readable data representing information including at least the victim's updated triage priority.

27. The method of claim 24, wherein said machine-readable two-dimensional symbology further represents information including at least one of: (1) the nature of the victim's injuries; (2) the victim's medical condition; (3) the victims initial treatment; and (4) the location to which the victim was transported or assigned.

* * * * *